(12) United States Patent
Dauster

(10) Patent No.: US 9,795,422 B2
(45) Date of Patent: Oct. 24, 2017

(54) ROD INSERTER, SYSTEM AND METHOD

(71) Applicant: AESCULAP IMPLANT SYSTEMS, LLC, Center Valley, PA (US)

(72) Inventor: Andrew Dauster, Breinigsville, PA (US)

(73) Assignee: AESCULAP IMPLANT SYSTEMS, LLC, Center Valley, PA (US)

( * ) Notice: Subject to any disclaimer, the term of this patent is extended or adjusted under 35 U.S.C. 154(b) by 66 days.

(21) Appl. No.: 14/989,356

(22) Filed: Jan. 6, 2016

(65) Prior Publication Data
US 2017/0189081 A1  Jul. 6, 2017

(51) Int. Cl.
A61B 17/70    (2006.01)

(52) U.S. Cl.
CPC ...... *A61B 17/7085* (2013.01); *A61B 17/7074* (2013.01); *A61B 17/7083* (2013.01); *A61B 17/7086* (2013.01)

(58) Field of Classification Search
CPC ............ A61B 17/7083; A61B 17/7085; A61B 17/7086; A61B 17/7088; A61B 17/7089
See application file for complete search history.

(56) References Cited

U.S. PATENT DOCUMENTS

| | | | |
|---|---|---|---|
| 6,530,929 B1 | 3/2003 | Justis et al. | |
| 7,008,422 B2 | 3/2006 | Foley et al. | |
| 7,011,660 B2 | 3/2006 | Sherman et al. | |
| 7,077,372 B2 | 7/2006 | Moran | |
| 7,188,626 B2 | 3/2007 | Foley et al. | |
| 7,520,879 B2 | 4/2009 | Justis et al. | |
| 7,648,506 B2 | 1/2010 | McCord et al. | |
| 7,648,507 B2 | 1/2010 | Techiera et al. | |
| 7,686,809 B2 | 3/2010 | Triplett et al. | |
| 7,717,944 B2 | 5/2010 | Foley et al. | |
| 7,763,055 B2 | 7/2010 | Foley | |
| 7,862,595 B2 | 1/2011 | Foley et al. | |
| 7,867,259 B2 | 1/2011 | Foley et al. | |
| 7,871,424 B2 | 1/2011 | Abdelgany | |
| 7,922,727 B2 | 4/2011 | Songer et al. | |

(Continued)

FOREIGN PATENT DOCUMENTS

| EP | 1221901 A1 | 7/2002 |
|---|---|---|
| EP | 1221901 B1 | 2/2007 |

(Continued)

*Primary Examiner* — Julianna N Harvey
(74) *Attorney, Agent, or Firm* — Kenealy Vaidya LLP

(57) ABSTRACT

A rod inserter, system and method can include an inserter that has a handle and an extension structure extending from the handle. A knob and a lever can be located adjacent the handle. A rod connection structure can be located at the distal end of the extension structure, and configured to rotate with respect to the extension structure. The rod connection structure can include a first clamshell structure and a second clamshell structure configured to move towards and away from each other in order to connect and disconnect from a rod, such as a spinal rod. The knob can be configured such that when actuated the first clamshell structure and second clamshell structure move with respect to each other. The lever can be configured such that when actuated the first clamshell structure and second clamshell structure are prevented from rotating with respect to the extension structure.

27 Claims, 7 Drawing Sheets

(56) References Cited

U.S. PATENT DOCUMENTS

| | | |
|---|---|---|
| 8,038,699 B2 | 10/2011 | Cohen et al. |
| 8,070,751 B2 | 12/2011 | Justis et al. |
| 8,100,909 B2 | 1/2012 | Butler et al. |
| 8,147,490 B2 | 4/2012 | Bauer |
| 8,182,509 B2 | 5/2012 | Abdelgany |
| 8,246,624 B2 | 8/2012 | Forton et al. |
| 8,343,160 B2 | 1/2013 | Techiera et al. |
| 8,361,124 B2 | 1/2013 | Sherman et al. |
| 8,721,685 B2 | 5/2014 | Foley et al. |
| 8,728,125 B2 | 5/2014 | Bruneau et al. |
| 8,900,275 B2 | 12/2014 | Justis et al. |
| 8,920,425 B2 | 12/2014 | Techiera et al. |
| 8,961,524 B2 | 2/2015 | Foley et al. |
| 2002/0161368 A1 | 10/2002 | Foley et al. |
| 2003/0060826 A1 | 3/2003 | Foley et al. |
| 2003/0229347 A1 | 12/2003 | Sherman et al. |
| 2005/0021031 A1 | 1/2005 | Foley et al. |
| 2005/0121576 A1 | 6/2005 | Moran |
| 2005/0131419 A1 | 6/2005 | McCord et al. |
| 2006/0111714 A1 | 5/2006 | Foley |
| 2006/0200135 A1 | 9/2006 | Sherman et al. |
| 2006/0229614 A1 | 10/2006 | Foley et al. |
| 2006/0265003 A1 | 11/2006 | Abdelgany |
| 2007/0185491 A1 | 8/2007 | Foley et al. |
| 2007/0198015 A1 | 8/2007 | Foley et al. |
| 2008/0077138 A1* | 3/2008 | Cohen .................. A61B 17/708 606/86 A |
| 2010/0094359 A1 | 4/2010 | Techiera et al. |
| 2010/0312279 A1 | 12/2010 | Gephart et al. |
| 2010/0331901 A1* | 12/2010 | Iott ..................... A61B 17/701 606/86 A |
| 2011/0071571 A1 | 3/2011 | Abdelgany |
| 2011/0106187 A1 | 5/2011 | Foley et al. |
| 2011/0152952 A1* | 6/2011 | Oh ..................... A61B 17/7085 606/86 A |
| 2011/0313460 A1* | 12/2011 | McLean ............. A61B 17/7032 606/264 |
| 2012/0029580 A1* | 2/2012 | Solitario, Jr. ...... A61B 17/7002 606/86 A |
| 2013/0053834 A1 | 2/2013 | Meyer et al. |
| 2013/0072987 A1 | 3/2013 | Justis et al. |
| 2013/0096626 A1 | 4/2013 | Techiera et al. |
| 2013/0150905 A1 | 6/2013 | Karpowicz |
| 2014/0046388 A1* | 2/2014 | Reichen ............. A61B 17/7083 606/86 A |
| 2014/0074106 A1* | 3/2014 | Shin .................. A61B 17/7079 606/104 |
| 2014/0155941 A1 | 6/2014 | Foley et al. |
| 2014/0249592 A1* | 9/2014 | Black ................. A61B 17/7004 606/86 A |
| 2014/0257416 A1 | 9/2014 | Meyer et al. |
| 2014/0336709 A1 | 11/2014 | Avidano et al. |
| 2015/0045842 A1 | 2/2015 | Justis et al. |
| 2015/0105832 A1* | 4/2015 | Gleason ............. A61B 17/7085 606/86 A |
| 2015/0157367 A1* | 6/2015 | Biedermann ...... A61B 17/7004 606/279 |
| 2015/0245856 A1 | 9/2015 | Gephart et al. |
| 2016/0038197 A1* | 2/2016 | Semingson .......... A61B 17/708 606/86 A |

FOREIGN PATENT DOCUMENTS

| | | |
|---|---|---|
| EP | 2234550 A1 | 10/2010 |
| EP | 2277468 B1 | 3/2012 |
| EP | 1737366 B1 | 12/2012 |
| EP | 2234550 B1 | 9/2014 |
| WO | 0128436 A1 | 4/2001 |
| WO | 2007090021 A1 | 8/2007 |
| WO | 2009083741 A1 | 7/2009 |

\* cited by examiner

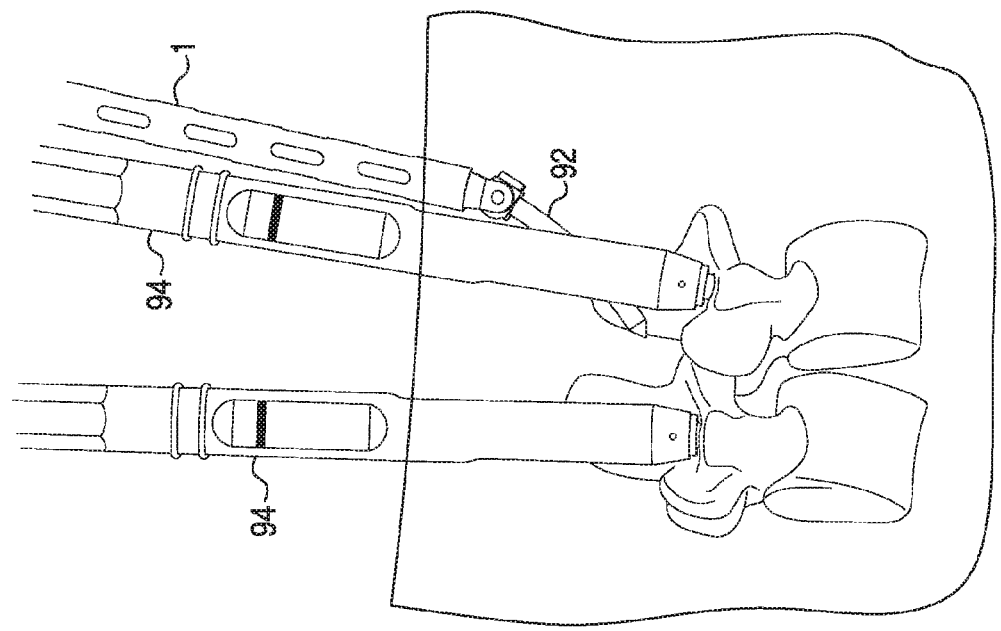
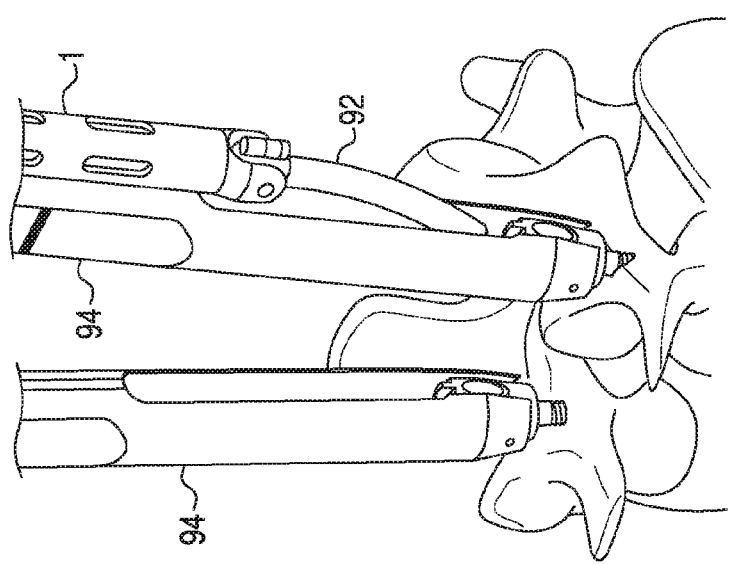

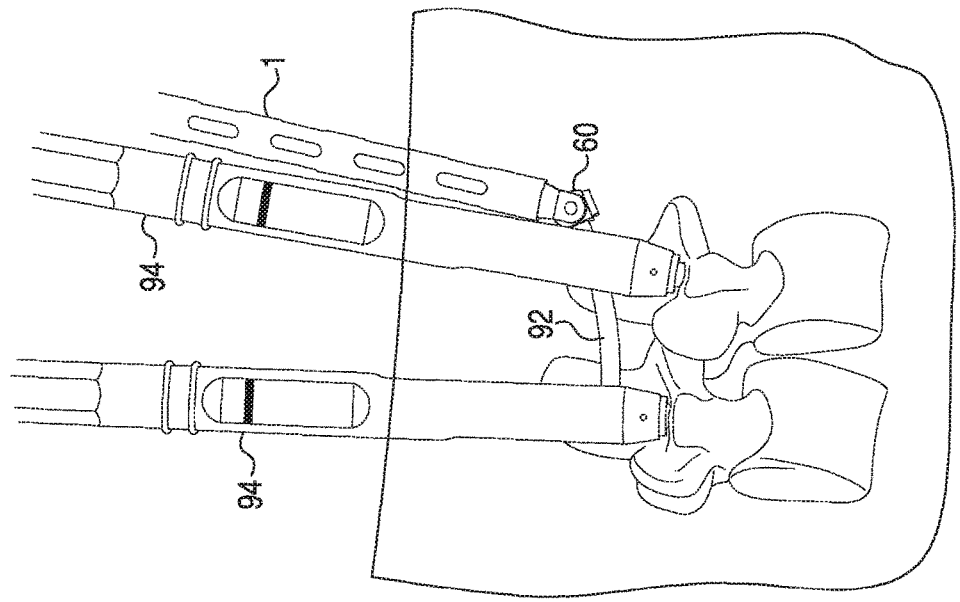
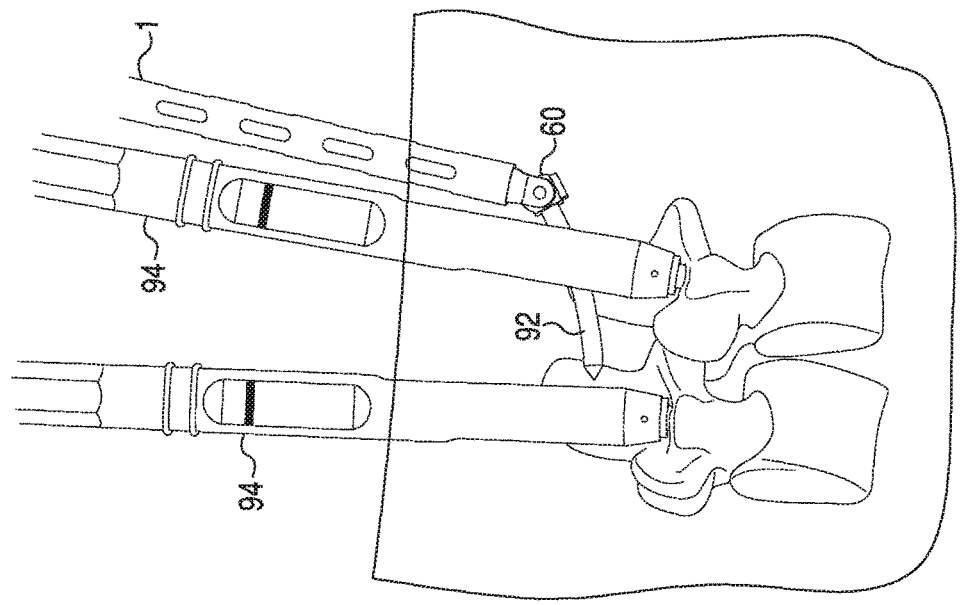

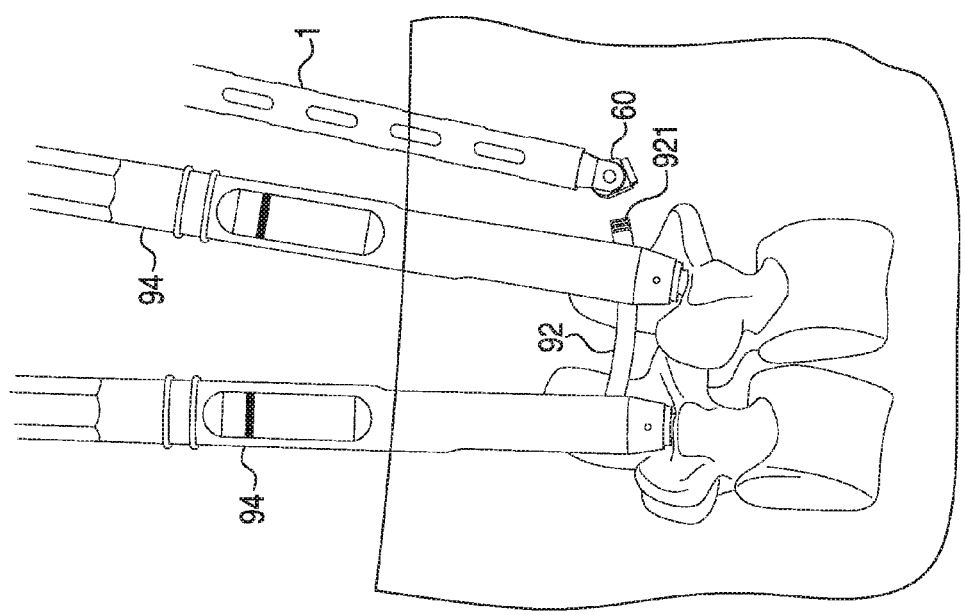

ROD INSERTER, SYSTEM AND METHOD

BACKGROUND

1. Field

The presently disclosed subject matter relates generally to surgical instrumentation devices, systems, and related methods, and more specifically to a rod inserter, system and method for use in placing, rearranging, and/or implanting a rod into a body, such as a spinal rod for placement adjacent to vertebrae of a spinal column.

2. Description of the Related Art

In order to stabilize the vertebrae of the spine, medical professionals have typically attached a stabilization rod along the spinal column using a series of pedicle screws attached to vertebrae. Each of the pedicle screws has a threaded portion and a head portion, with the threaded portion including screw threads that can grip each separate vertebrae. The head of the pedicle screw can include a rod receiver, which can be configured in various manners, such as a saddle or U-shaped aperture which receives the spinal rod therein. Also, set screws can be used to lock the spinal rod into the saddle or U-shaped aperture of each of the pedicle screws. Of course, other shaped openings can be used on the pedicle screw for placement of the spinal rod.

During implantation or other manipulation of the spinal rod and system, a rod inserter is commonly used to insert the spinal rod into the rod receiver structure located at the head of each pedicle screw. In general, alignment of the rod into each of the series of pedicle screws can be difficult to accomplish due to space requirements, variation in alignment of the pedicle screws, and the amount of force required to manipulate and/or bend the spinal rod. A rod inserter is often used to accomplish this task. There has been a longfelt need for the rod inserter to attach and detach quickly and securely to an end of the rod that is being implanted, while also providing a certain degree of movement and manipulation ability of the rod when the rod is being securely held by the rod inserter.

Conventional rod inserters have included devices that are bulky and have limited degrees of motion, while also requiring greater movement on the part of the operator to couple to a rod, such as a spinal rod, and to manipulate the spinal rod.

SUMMARY

Accordingly, it may be beneficial to provide a rod inserter device, system, and method that requires minimal space, is easily and accurately operated, and is also easily dismantled for cleaning, inspection, etc. In addition, a need has been uncovered for a device that uses a fundamentally different operating strategy for each of the different operational functions. Moreover, a rotational operation can be used to secure the rod to a rod connection structure located on the rod inserter, and a different rotational movement of a second structure can then be used to rotationally lock the rod connection structure with respect to a remainder of the rod inserter. Thus, the fundamental motion used to cause operation for each of these functions is different and can be easily understood and distinguished by a user, and can be easily accomplished in an ergonomic manner at two locations adjacent a handle of the rod inserter.

The rod inserter can be used in surgery, for example, during placement of a rod adjacent a bone. In particular, the rod inserter can be used to implant a spinal rod for posterior fusion of the spine.

According to an aspect of the disclosed subject matter, the rod inserter can be helpful when fitting a spinal rod to a pedicle screw(s) in the spine, especially when the rod is difficult to place in the screw head. The difficulty of placing the rod in the screw head is quite common for long fusion cases where multiple polyaxial screws are joined in a row or series by one rod and especially when the screws are at slightly different heights relative to the bone in which they are inserted.

The streamlined shape of the rod inserter enables the rod inserter to be used without making a larger incision than is necessary to insert the rod. The inventive rod inserter of the instant application can therefore be used during less invasive operations which have been shown to reduce patient trauma. The rod inserter is designed for ease of use.

The presently disclosed subject matter allows for the controlled detachment of a rod at any articulated position. In addition, articulation is managed in a different manner in the instrument according to the presently disclosed subject matter. In particular, certain embodiments can have driven articulation, for example, where a handle is pulled the rod is articulated from a vertical position to a horizontal position. By contrast, in the presently disclosed subject matter, an embodiment is disclosed in which articulation can be passive in nature, where the surgeon releases a brake and allows the rod to move.

The instrument is designed to be cleanable by disassembling the various components after use. The instrument can also include several opening into and through which steam and/or cleaning fluids are easily penetrable.

According to one aspect, a rod inserter for inserting a rod can include a handle having a proximal end and a distal end, an extension structure extending from the handle, the extension structure having a distal end, a proximal end, and a longitudinal axis, a first motion structure disposed intermediate the proximal end of the handle and the distal end of the extension structure, and a rod connection structure located at the distal end of the extension structure, the rod connection structure configured to rotate with respect to the extension structure, and to move toward and away from the longitudinal axis of the extension structure in order to connect and disconnect from the rod. The first motion structure can be configured to move the rod connection structure toward the longitudinal axis of the extension structure when actuated. The rod inserter can also include a second motion structure configured to prevent the rod connection structure from rotating with respect to the extension structure when actuated.

In accordance with yet another aspect of the disclosed subject matter, a rod inserter for inserting a rod can include a handle having a proximal end, a distal end, and a longitudinal axis, a lever actuation structure located adjacent the handle and having a rotational axis that is at an angle relative to the longitudinal axis of the handle, an extension structure extending from the handle, the extension structure having a distal end, a proximal end, and an extension structure longitudinal axis, a knob actuation structure located between the proximal end of the handle and the distal end of the extension structure, and a rod connection structure located at the distal end of the extension structure. The rod connection structure can be configured to rotate about a rotational axis and with respect to the extension structure, and the rod connection structure can include a first clamshell structure and a second clamshell structure, wherein the first clamshell structure and second clamshell structure are configured to move towards and away from each other in order to connect and disconnect from the rod, and wherein the knob actuation structure is configured such that when actuated in a first direction the first clamshell structure and the second clamshell structure move toward each other, and when actuated in a second direction different from the first direction, the first clamshell structure and the second clamshell structure move away from each other. The lever actuation structure can be configured such that when actuated the first clamshell structure and second clamshell structure are prevented from rotating about the rotational axis of the rod connection structure.

In accordance with still another aspect of the disclosed subject matter, a method of using a rod inserter can include providing a rod inserter including, a handle having a proximal end, a distal end, and a longitudinal axis, a knob located adjacent the handle and having a rotational axis, a lever located adjacent the handle and having a rotational axis, an extension structure extending from the handle, the extension structure having a distal end, and a proximal end, and a rod connection structure located at the distal end of the extension structure, the rod connection structure configured to rotate with respect to the extension structure. The method of using a rod inserter can further include actuating the lever to prevent the rod connection structure from rotating with respect to the extension structure. The method of using a rod inserter can further include actuating the knob to cause a first portion of the rod connection structure to move with respect to the extension structure in a first direction, and to cause a second portion of the rod connection structure to move with respect to the extension structure in a second direction different from the first direction.

BRIEF DESCRIPTION OF THE DRAWINGS

The disclosed subject matter of the present application will now be described in more detail with reference to exemplary embodiments of the apparatus, system and method, given by way of example, and with reference to the accompanying drawings, in which:

FIG. 6C is a perspective view of the rod inserter of FIG. 1 depicting a method of using the rod inserter.

FIG. 6D is a perspective view of the rod inserter of FIG. 1 depicting a method of using the rod inserter.

FIG. 6E is a perspective view of the rod inserter of FIG. 1 depicting a method of using the rod inserter.

FIG. 6F is a perspective view of the rod inserter of FIG. 1 depicting a method of using the rod inserter.

FIG. 6G is a perspective view of the rod inserter of FIG. 1 depicting a method of using the rod inserter.

DETAILED DESCRIPTION OF EXEMPLARY EMBODIMENTS

A few inventive aspects of the disclosed embodiments are explained in detail below with reference to the various figures. Exemplary embodiments are described to illustrate the disclosed subject matter, not to limit its scope, which is defined by the claims. Those of ordinary skill in the art will recognize a number of equivalent variations of the various features provided in the description that follows.

Figure 1:
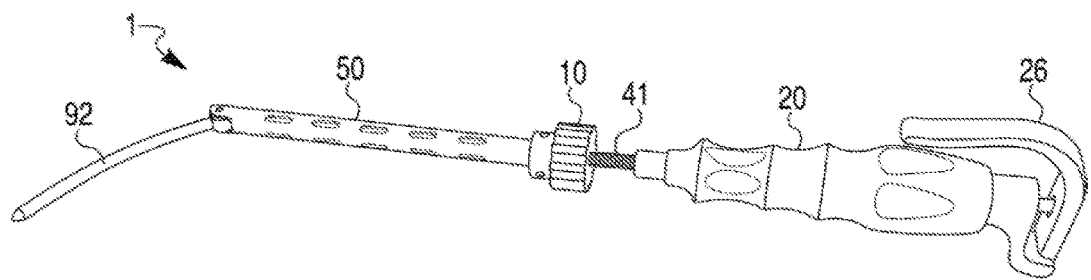
FIG. 1 is a perspective view of an example of a rod inserter device made in accordance with principles of the disclosed subject matter.

FIG. 1 illustrates an embodiment of a rod inserter 1 for inserting a rod 92 into a patient made in accordance with principles of the disclosed subject matter. For example, the rod inserter 1 can be configured to be an instrument for use with the rod 92 in a rod-based pedicle screw system. The rod inserter 1 can include a handle 20, a linkage that can be formed in various manners, such as threaded shaft 40, and an outer shaft 50. The rod inserter can include a first motion structure configured in various forms, such as a knob 10, located adjacent the handle 20. The rod inserter can also include a second motion structure configured in various forms, such as a lever 26, located adjacent the handle 20. In the present embodiment, the threaded shaft 40 extends from a distal portion of the handle 20 and within the outer shaft 50, and the knob 10 is disposed at an end of the outer shaft 50 proximate the handle 20. The outer shaft 50 can be configured to move as an outer sleeve longitudinally along threaded shaft 40 via rotation of the knob 10 such that the outer shaft 50 is moved relative to the handle 20. In addition, outer shaft 50 can be rotatable with respect to the knob 10 via a bearing located therebetween, or can be attached to or formed with the knob 10 such that knob 10 and outer shaft 50 rotate with each other. If the outer shaft 50 is rotatable with respect to the knob 10, then the outer shaft 50 can be splined in some manner to prevent rotation of the outer shaft 50 with respect to other structures, such as the handle 20 or a rod connection structure located at a distal end of the rod inserter 1. Alternatively, the outer shaft 50 can be a separate structure that is "pushed" along a longitudinal axis of the rod inserter 1 by the knob 10 when the knob 10 is rotated. The rod connection structure can be separated from the handle 20 by an extension structure that can be formed in various manners and can include any of the structures that extend from the handle 20 to the rod connection structure of the present embodiment.

The second motion structure of the rod inserter 1 of the present embodiment can be configured, for example, as a lever 26 hingedly attached to an end of the rod inserter 1 and at a proximate end of the handle 20. Together with the handle 20, the lever 26 may serve to hold and control the rod inserter 1, as well as apply load to the rod 92. The lever 26 can be configured to permit or prohibit pivoting of the rod 92 by the rod inserter 1 so as to allow for dynamic insertion of the rod 92 into the patient. The lever 26 of the present embodiment may be formed of metal, however other materials such as plastics may be appropriate for some embodiments.

Figure 2:
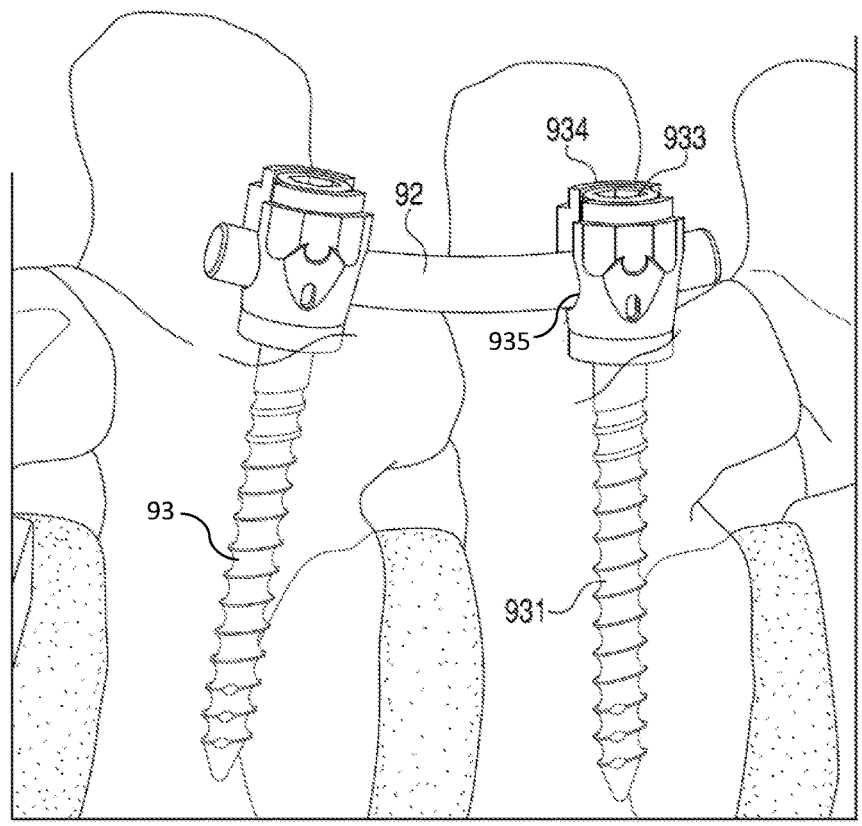
FIG. 2 is a perspective view of an exemplary rod located within pedicle screws along a patient's spine.

FIG. 2 illustrates exemplary pedicle screws 93 into which the rod 92 may be inserted using the rod inserter 1 in accordance with principles of the disclosed subject matter. The screws 93 may be polyaxial or monoaxial screws configured for use in the spine for stabilization in spine fixation, particularly bony fusion. Alternatively, the screws 93 may be configured as anchor points for a dynamic system. To create the anchor points with the screws 93, the screws 93 can be inserted into bone through pedicles of the respective vertebrae. Each screw 93 includes threads 931, a throughway 935, internal threads 933 located at a top portion of the throughway 935, and a set screw 934. Insertion of the screws 93 into a patient can be through a posterior approach, for example, to the thoraco-lumbar spine, such that the threads 931 can be screwed into vertebrae of the patient. The internal threads 933 can be configured to receive the respective set screw 934 to secure the rod 92 within the throughway 935. The throughway 935 can be configured as a saddle or U-shaped aperture so as to accommodate insertion of the rod 92.

In the present embodiment, the screws 93 are initially screwed into vertebrae of the patient. The screws 93 may be screwed into adjacent or consecutive vertebrae, however other combinations of vertebrae may be joined via insertion of the rod 92. With the screws 93 properly positioned in the vertebrae, the rod 92 can be inserted through the throughways 935 of the respective screws 93. Based on the disposition of the vertebrae and screws, the rod 92 may be curved or bowed to be insertable into the throughways 935, however, the rod 92 may also otherwise be straight. To secure the rod 92 once it has been inserted into the throughways 935, the set screws 934 are screwed into the internal threads 933 of the respective screws 93 and/or rod persuader tools can be used to set the rod 92 in place via the upper opening (when the set screw 934 is not yet in place) in the saddle or U-shaped aperture of the screw 93. Once the rod is properly located in the saddle or U-shaped aperture of the screw 93, screwing the set screws 934 compresses the rod 92 into the throughways 935 to lock down the rod 92 and secure it against movement of the vertebrae or screws 93. Once secured, the rod 92 can serve as a rigid bridge between the screws 93 configured as anchors in the vertebrae. The exemplary rod 92 in FIG. 2 is shown connecting a pair of vertebrae via the screws 93, however the rod inserter 1 may be configured to insert a rod 92 for connecting any number of vertebrae via respective screws, such as one, two, three, four, five, etc.

Figure 3:
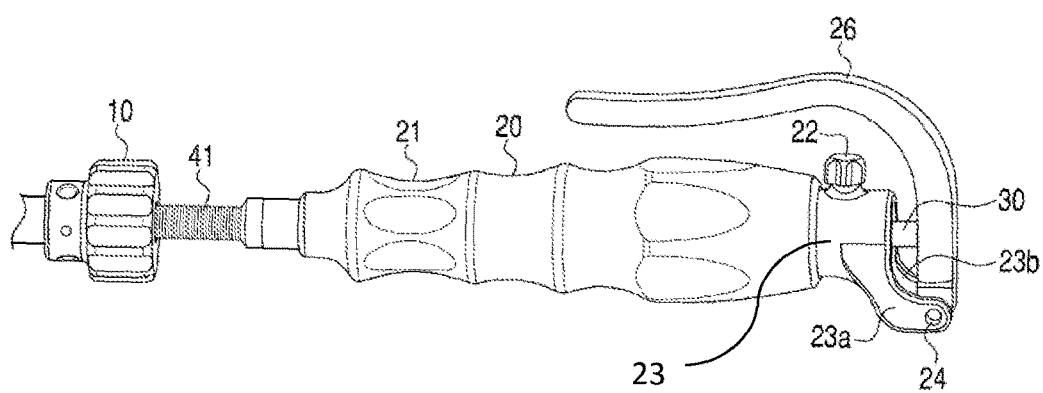
FIG. 3 is a partial perspective view of a proximal portion of the rod inserter of FIG. 1.

FIG. 3 illustrates an embodiment of a handle side of the rod inserter 1 in accordance with principles of the disclosed subject matter. The handle 20 of the present embodiment is disposed between the threaded shaft 40 and the lever 26, the handle 20 can include a grip portion 21 with several contours and indents such that the handle is configured to be gripped by a hand of an operator using the rod inserter 1. The grip portion 21 can have ridges, dimples, rings, collars, or any other configuration of edges and surfaces contoured for gripping.

In the present embodiment, the lever 26 can be hingedly attached to a collar 23 disposed adjacent the handle 20, the collar 23 connecting the lever 26 to the handle 20. The lever 26 shown in FIG. 3 is attached to the collar 23 via a pin 24 inserted through a pair of collar arms 23a and 23b. The collar arms 23a,b can extend around opposing sides of an end of the lever 26. The lever 26 can be contoured so as to curve around a proximate end of the handle 20, extending to an intermediate portion of the handle 20 before terminating. As the lever 26 contours around the proximate end of the handle 20, the lever 26 remains spaced from the handle 26. The lever 26 can be actuated at any portion, including a portion of the lever 26 extending along and approximately parallel to a direction of elongation of the handle 20. As described in more detail below, applying a squeezing force to the lever 26 can transmit load to the inner shaft 30 of the rod inserter 1 which extends slightly out of the proximal most portion of the handle 20 such that the lever 26, when actuated, rotates about pin 24 and contacts the inner shaft 30 to move the inner shaft 30 relative to the handle 20 and relative to the threaded shaft 40 and outer shaft 50.

In the present embodiment, the lever 26 may be fixedly attached to the handle 20 by a set screw 22 such that the lever is rotatable about the longitudinal axis of the rod inserter 1. In order to rotate the lever 26 around the rod inserter 1, the set screw 22 disposed at a portion of the rod inserter 1 between the handle 20 and the collar 23 is released. The set screw 22 abuts against a portion of handle 20 that is located within the collar 23 such that the collar 23 and handle are locked together by frictional force when the set screw 22 is tightened (i.e., rotated so as to extend into and contact the portion of handle 20 located within collar 23). Once the set screw 22 has been released (e.g., rotated counterclockwise to back out of contact with the portion of handle 20 located within collar 23), the lever 26 and collar 23 can rotate about the longitudinal axis of the handle 20, and can be removed from handle 20 altogether. After rotation and/or removal, the lever 26 can then be locked back into a new position with respect to the handle 20 of the rod inserter 1 by tightening the set screw 22. Rotation of the lever 26 about the handle 20 of the rod inserter 1 allows for use at various angles with respect to the rod 92 (that is connected at a distal portion of the rod inserter 1), and therefore provides increased orientations for use, and greater ability for adaptation for both left and right handed users during use. For example, if a user of the rod inserter 1 starts placement of a rod 92 into a patient, and arrives at a position in which operation of the lever 26 or other actuation device is preferred to be arranged at a different location (in order to provide more leverage when using the device, or to allow a left handed user to step in at that point), the set screw can be backed out at that time and the collar 23 (and lever 26) can be moved to a different position with respect to both the rod 92 that is now in a particular position within the patient, and the other actuation device(s) that may be located on the rod inserter 1. The lever 26 and collar 23 can then be re-affixed or locked with respect to the handle 20 and rod 92, and a user can then continue with the method or procedure with the lever 26 and rod inserter 1 differently configured and locked in place at the new position.

Moreover, the set screw 22 can be released by unthreading it from the collar 23. The set screw 22 can be configured to engage divots located within the handle structure 20 to prevent the relative rotation of the collar 23 and the handle 20 when the set screw is engaged. Partial unthreading of the set screw allows the collar 23 to rotate into a different position, allowing for use by left and right handed people. It is not necessary to provide direct connection or interaction between screw 22 and the inner shaft 30.

The lever 26 of the present embodiment can be configured to contact an end of the inner shaft 30, the inner shaft 30 extending through hollow interior portions of both the handle 20 and the threaded shaft 40. The inner shaft 30 can be a tube or a rod of circular, elliptical or polygonal cross section, and can be configured to slide longitudinally along the hollow interior portions of the handle 20 and the threaded shaft 40 via rotation of the lever 26. Rotation of the lever 26 pushes the inner shaft 30 towards the rod end (distal end) of the rod inserter 1 via contact between the contact area of the lever 26 and the proximal most end of the inner shaft 30.

Additionally, the present embodiment of FIG. 3 includes the knob 10 shown concentrically surrounding the threaded shaft 40. The knob 10 can have threads engaged with the threads 41 of the threaded shaft 40 such that the knob 10 is configured to rotate about the threaded shaft 40 as corresponding threads facilitate screw-like movement. An exterior portion of the knob 10 may be ribbed or otherwise include grooves so as to be readily gripped for rotating. A bearing can be located between the knob 10 and the outer shaft 50 to facilitate relative rotation between the knob 10 and outer shaft 50 while allowing both the knob 10 and outer shaft 50 to move relative to the threaded shaft 40 when the knob 10 is rotated.

Figure 4:
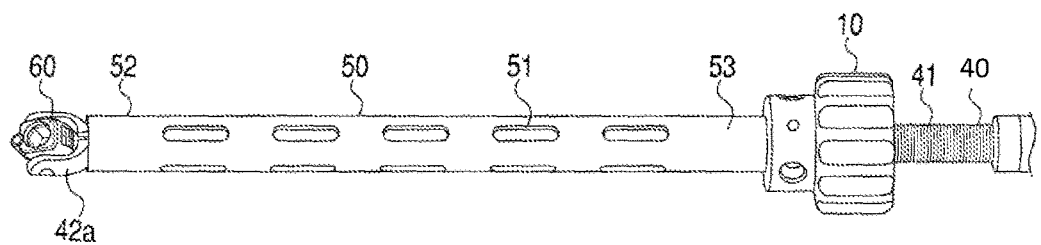
FIG. 4 is a partial perspective view of a distal portion of the rod inserter of FIG. 1.

FIG. 4 illustrates an embodiment of a rod side of the rod inserter 1 in accordance with the principles of the disclosed subject matter. The outer shaft 50 of the present embodiment is disposed to concentrically surround the threaded shaft 40 from the knob 10 to a rod connection structure, for example, a clamping head 60 located at the rod end of the rod inserter 1. The outer shaft 50 can be cylindrically shaped and hollow to accommodate the threaded shaft 40 extending within, and may also include openings 51 extending along its length from a first end 52 to a second end 53. The openings 51 can be elliptical, rectangular, or any other appropriate shape. The openings 51 of the present embodiment are spaced both longitudinally and circumferentially from each other, and can facilitate cleaning of the device while also reducing weight of the device.

The threaded shaft 40 of the present embodiment extends beyond the first end 52 of the outer shaft 50 to reveal a collet 42*a*, the clamping head 60 being accommodated within the collet 42*a*. As described below, clamping the rod 92 is actuated by design of the collet 42*a*. Rotating the knob 10 moves the first end 52 of the outer shaft 50 towards the collet 42*a*, which contracts and is thereby configured to squeeze the clamping head 60 together. The above described axial motion of the outer shaft 50 is thereby transformed into a compression motion by the interaction of the outer shaft 50 on the collet 42*a*. Although the collet 42*a* in the present embodiment is actuated by a nut, other actuations may be suitable in alternative embodiments, such as a lever, ratchet, gear, etc. The collet 42*a* and the clamping head 60 serve to form a releasable and lockable connection between the rod inserter 1 and the rod 92.

The clamping head 60 of the present embodiment is disposed within a collet 42*a* at an end of the threaded shaft 40. As described below, the collet 42*a* is at a portion of the threaded shaft 40 that extends beyond the first end 52 of the outer shaft 50.

Figure 5A:
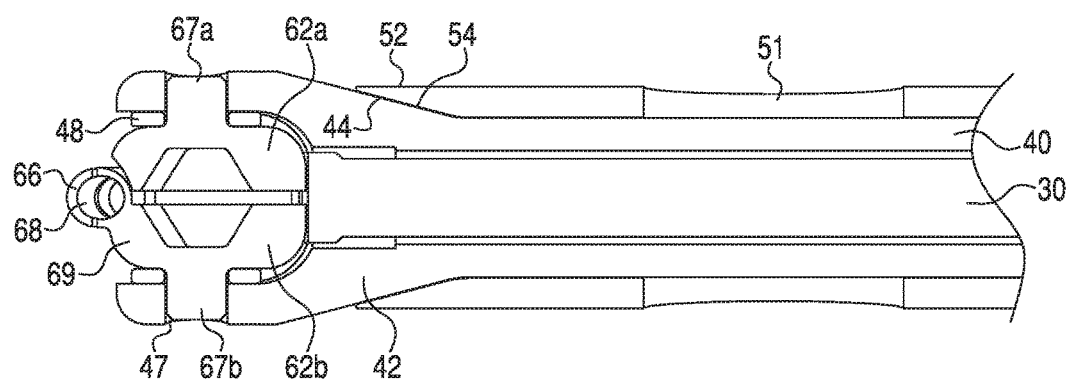
FIG. 5A is a cross sectional view of a distal portion of the rod inserter of FIG. 1 taken along VA-VA of FIG. 4.

FIG. 5A illustrates a cross section of an embodiment of the rod side of the rod inserter 1 in accordance with principles of the disclosed subject matter. The first end 52 of the outer shaft 50 is shown surrounding the threaded shaft 40, which in turn surrounds the inner shaft 30. In the first end 52, the openings 51 reveal an outer surface of the threaded shaft 40. A terminal portion of the first end 52 also includes a taper 54, the taper 54 transitioning from a first inner diameter of the outer shaft 50 to a second inner diameter, the second inner diameter being greater than the first. Therefore, an inner diameter of the first end 52 widens at the terminating portion. In the present embodiment, the taper 54 of the first end 52 corresponds to a taper surface 44 of the threaded shaft 40, with the taper surface 44 widening in accordance with the taper 54. The taper 54 and the taper surface 44 are tapered at approximately corresponding angles, however their angles of taper may vary to a degree so as to avoid taper lock characteristics.

The linkage formed as shaft 40 in this embodiment has an outermost diameter at its distal end that is larger than an outermost diameter of the outer shaft 50. This relationship can be seen just to the left of distal end 52 of the outer shaft 50 as shown in FIG. 5A.

The present embodiment of the rod inserter 1 includes the collet 42*a* disposed at the first end 42 of the threaded shaft 40, as described above. The collet 42*a* is formed with the taper surface 44, and is disposed adjacent and can extend beyond the first end 52 of the outer shaft 50. Opposing sides of the collet 42*a* can include openings 47 through which first and second axle extensions 67*a,b* of the clamping head 60 extend so as to secure the clamping head 60 within the collet 42*a*, as described below. The openings 47 may be cylindrical or otherwise complementary in shape to the first and second axle extensions 67*a,b*. The collet 42*a* can also include a pair of bearings 48 disposed adjacent interior surfaces of the opposing sides of the collet 42*a*. The bearings 48 also encircle the respective first and second axle extensions 67*a,b*, preventing the interior surfaces of the collet 42*a* from directly contacting top and bottom clamshell portions 62*a,b* of the collet 42*a*, as described below. Compression of the outer shaft 50 on the collet 42*a* in turn squeezes on the bearings 48, forcing the clamping head 60 closed, as described below. The bearings 48 of the present embodiment can be polyether ether ketone (PEEK) bearings, however configurations of rubber, metal, plastic or ceramic may be appropriate for some embodiments. The above described configuration of the clamping head 60 and the collet 42*a* allow the rod inserter 1 to clamp onto the rod 92 without limiting rotation of the rod 92, which is described in more detail below. Moreover, the rod 92 may rotate freely relative to other portions of the rod inserter 1, and specifically relative to the collet 42*a* and handle 20, when the rod 92 is locked within the clamping head 60.

As described above, the clamping head 60 is disposed within the collet 42*a* via insertion of the first and second axle extensions 67*a,b* within the openings 47. The rod inserter 1 may therefore include the clamping head 60 configured to pivot about a rotational axis defined by the first and second axle extensions 67*a,b*. The clamping head 60 of the present embodiment includes the top and bottom clamshell portions 62*a,b*, from which the first and second axle extensions 67*a,b* extend, respectively. Each of the top and bottom clamshell portions 62*a,b* include respective halves of a hex opening 69, such that cross sections of the respective halves of the hex opening 69 are approximately trapezoidal. Although not required, in one embodiment the clamping head 60 can also include a hinge 66 configured to join the top clamshell portion 62*a* to the bottom clamshell portion 62*b* at a side of the clamping head 60. The hinge 66 may be configured as a barrel hinge to include an opening through hinge 68, or may alternatively be configured as a living hinge or any other appropriate type of hinge. Of course, no hinge is necessary in the clamping head 60 and the two clamshell portions can be connected by a single continuously molded structure. The clamping head 60 can also be held in a uniform relative position to surrounding elements by the hinge 66. In some embodiments, the hinge 66 may include a floating hinge. The hinge 66 is configured to cause the top and bottom clamshell portions 62*a,b* to move in a substantially linear motion towards and away (together and apart) as a result of being compressed and released by the collet 42*a*, as described below. Although, it should be noted that depending on the type of hinge 66 incorporated into the structure, the motion of the top and bottom clamshell portions 62*a,b* can strictly be considered to be rotational. Thus, the substantially linear motion should be considered to include this type of rotational motion (having a relatively large center of rotation) between the top and bottom clamshell portions 62*a,b* such that, in effect, the top and bottom clamshell portions 62*a,b* basically move toward and away from each other. The collet 42a of the present embodiment has a spring back bias such that opposing sides of the collet 42a can return to a pre-compressed state when the outer shaft 50 is moved away from the collet 42a by virtue of rotating the knob 10. Clamping and release of the rod 92 is thereby dependent upon corresponding motion of opposing sides of the collet 42a, and specifically, release of the rod 92 from the clamping head 60 may be dependent upon spring back of the collet 42a.

In the present embodiment, the outer shaft 50 and/or the knob 10 can have a threaded interior portion to engage the threads 41 of the threaded shaft 40. The outer shaft 50 can therefore be moved longitudinally along the threaded shaft 40 through rotation of the knob 10, which effectively screws either the outer shaft 50 or the knob 10, or both, along the threads 41. If the knob 10 is rotated so as to move the outer shaft 50 towards the clamping head 60, the taper 54 of the first end 52 contacts the taper surface 44 and displaces the first end 42 of the threaded shaft 40. As the first end 42 is displaced, the opposing sides of the collet 42a correspondingly displace and clamp together, thereby exerting a compressive force on the top and bottom clamshell portions 62a,b of the clamping head 60 (via the bearings 48). When compressed, the top and bottom clamshell portions 62a,b move towards each other while also being able to rotate together about the hinge 66 via bearing 48, thus clamping the halves of the hex opening 69 together. Clamping the hex opening 69 can secure an end of the rod 92 within the hex opening 69 and facilitate insertion of the rod 92 into the patient. The hex opening 69 of the present embodiment is configured to prevent axial roll of the rod 92, especially with use of a rod having a hex-shaped connection end. In some embodiments, geometry of an opening in the clamping head 60 and an engageable end of the rod 92 may be varied so as not to be hex-like yet still able to prevent roll, such as by being otherwise polygonal or elliptical. Furthermore, some embodiments may include additional opening geometry and corresponding rod end geometry to increase axial pull-out of the rod, for example, a lip and annular groove structure could be provided to enhance axial locking if desired.

The rod inserter 1 of the present embodiment also includes the inner shaft 30 extending through the hollow portion of the threaded shaft 40. As described above, the inner shaft 30 extends from the lever 26, through the handle 20 and the threaded shaft 40 to the collet 42a. The inner shaft 30 is configured to be movable within the hollow portion of the rod inserter 1 so as to be brought into contact with the clamping head 60 upon actuation of the lever 26. As described below and shown in FIG. 5B, an end of the inner shaft 30 that is brought into contact with the clamping head 60 can be configured to grip the clamping head 60 to prevent its rotation within the collet 42a.

Figure 5B:
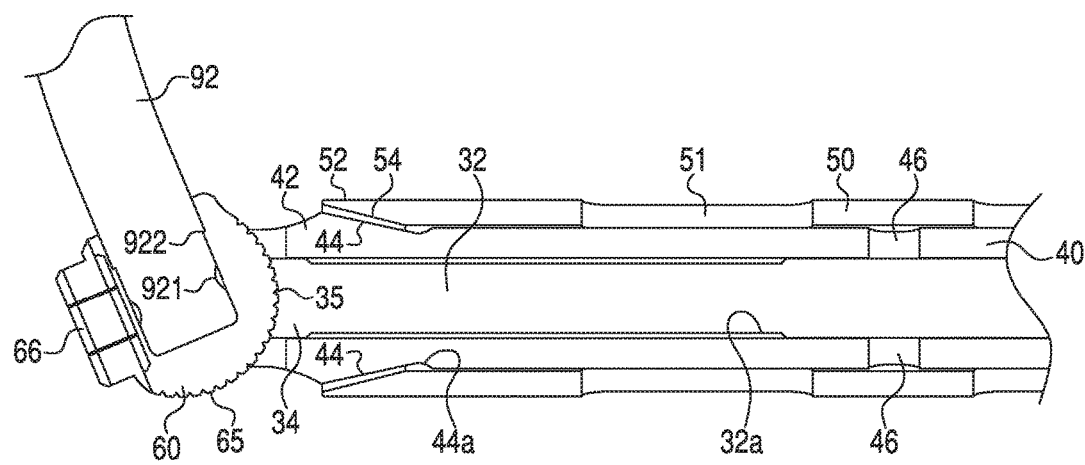
FIG. 5B is a cross sectional view of a distal portion of the rod inserter of FIG. 1 taken along VB-VB of FIG. 4.

FIG. 5B illustrates a cross section view of an embodiment of the rod side of the rod inserter 1 in accordance with principles of the disclosed subject matter. The threaded shaft 40 can include openings 46 provided at opposing sides to allow for cleaning of the rod inserter 1, the openings 46 being approximately cylindrical apertures extending through the sides of the threaded shaft 40. The threaded shaft 40 can also include a bevel 44a disposed adjacent the taper surface 44, the bevel 44a configured to wrap around and be located adjacent an inner circumference of the outer shaft 50. Specifically, the bevel 44a is disposed adjacent a narrow portion of the taper surface 44 spaced from the terminating portion of the outer shaft 50 and a wide portion of the taper surface 44. The bevel 44a can be configured to provide clearance for the tapered first end 52 of the outer shaft 50 such that a taper lock can be prevented between the threaded shaft 40 and the outer shaft 50. The bevel 44a can also be configured to act as a stopper so that the first end 52 of the outer shaft 50 does not move past the first end 42 of the threaded shaft 40 and interfere with operation of the collet 42a.

In the present embodiment, a distal end of the inner shaft 30 that is brought into contact with the clamping head 60 is configured to grip the clamping head 60 to prevent its rotation within the collet 42a. Rotation of the rod 92 is therefore controlled by the inner shaft 30 which prevents rotation of the clamping head 60. Regarding attachment and detachment of the rod 92 to and from the clamping head 60, angulation of the rod 92 does not affect retention of the rod 92 within the clamping head 60, and the rod 92 may be attached or detached at any angulation of the clamping head 60 within the collet 42a. As described above and shown in FIG. 5B, the clamping head 60 is configured to rotate within the collet 42a via rotation of the first and second axle extensions 67a,b within the openings 47. The clamping head 60 may therefore include a textured surface 65 disposed around an outer surface of the clamping head 60, the textured surface 65 extending from the hinge 66 to the hex opening 69. The textured surface 65 can include teeth, ridges, dimples or any other type of surface configured for gripping a head 34 of the inner shaft 30 when the inner shaft 30 is pressed into contact with the clamping head 60 by actuation of the lever 26. Force from the lever 26 can thereby be transmitted down the inner shaft 30 to prevent rotational motion of the clamping head 60. The head 34 of the inner shaft 30 can also include a textured surface 35 to grip the textured surface 65 of the clamping head 60 when the two are brought into contact. The textured surface 35 can be configured to complement the teeth, ridges or dimples of the textured surface 65 of the clamping head 60. Interdigitating of the inner shaft 30 with the clamping head 60 allows the rod 92 to be held steady as it is forced through soft tissue of the patient by the operator of the rod inserter 1. Alternatively, mating geometry between the textured surfaces 35,65 of the inner shaft 30 and the clamping head 60, respectively, may take multiple other forms that are appropriately configured to allow the inner shaft 30 to prevent rotation of the clamping head 60 at certain intervals or upon a continuum of motion.

The lever 26 of the rod inserter 1 is actuable so as to apply and release pressure on the inner shaft 30, which thereby transfers that application and release of pressure to the clamping head 60 (as can be seen in the exemplary method of use depicted in FIGS. 6A-G). When a requisite amount of pressure is applied to the lever 26 and transmitted through the inner shaft 30 to the clamping head 60, the interdigitations of the clamping head 60 and the inner shaft 30 are loaded in shear and the clamping head 60 is locked at a corresponding angle of rotation within the collet 62a. The clamping head 60 is thereby prevented from pivoting when loaded by the lever 26. When a requisite amount of pressure is released from the lever 26, the clamping head 60 and the inner shaft 30 are released from shear loading and the clamping head 60 may rotate relatively freely, absent other obstructions. The inner shaft 30 is thereby forced away from the pivoting clamping head 60 when not loaded by the lever, releasing angulation of the clamping head 60. The above described interaction between the clamping head 60 and the inner shaft 30 permits controlled passive rotation of the rod 92, allowing desirable control over the locking and unlocking of angulation of the clamping head 60, as described in more detail below and shown with respect to the exemplary method depicted in FIGS. 6A-G.

The inner shaft 30 of the present embodiment can also include a smaller width portion 32a that has a decreased diameter compared to adjacent portions of the inner shaft 30. The smaller width portion 32a can be disposed at the first end 32 between the openings 46 of the surrounding threaded shaft 40 and the head 34. Alternatively, the smaller width portion 32a can be disposed anywhere along the inner shaft 30. The smaller width portion(s) 32a can reduce relative friction to facilitate movement of the inner shaft 30 with respect to the threaded shaft 40, and can also provide space (for steam or other cleaning fluid) to facilitate cleaning of the rod inserter 1. The inner shaft 30 can be removed for cleaning. The smaller width/diameter portion 32a can be used for functional reasons, such as clearance for clamping head 60.

Since the rod 92 is inserted and clamped within the clamping head 60, any rotation of the clamping head 60 yields corresponding rotation of the rod 92. To ensure that the rod 92 rotates accordingly, the rod 92 can be provided with an end geometry 921 configured to hold an end of the rod 92 within the clamping head 60 throughout rotation. The end geometry 921 can include one or more ridges, bumps or dimples configured to engage a complementary opening geometry of the hex opening 69 to secure the rod 92. In addition, the overall shape of a portion 922 of the rod 92 that is to be connected with the clamping head 60 can specifically mate with the shape of the clamping head 60. For example, when the opening in the clamping head 60 is hexagonal, the portion 922 of rod 92 can also be hexagonal (or other shape depending on application and user preference).

FIG. 6A-G illustrate an exemplary method of use of the rod inserter 1 at various stages of insertion of the rod 92 into the patient (and, for example, into pedicle screws 93). As shown in FIGS. 6A-G, downtubes 94 are attached to the screws 93 such that a portion of each downtube 94 is inserted within the patient, while another portion remains outside of the patient. The downtubes 94 can be removably attached to the screws 93 by any appropriate method including screwing, clamping, etc.

Figure 6A:
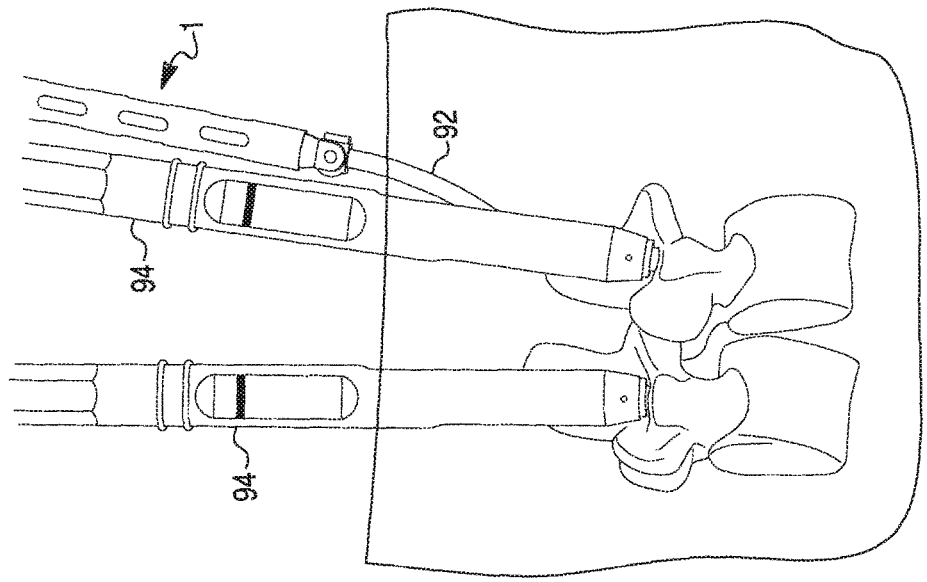
FIG. 6A is a perspective view of the rod inserter of FIG. 1 depicting a method of using the rod inserter.

In FIG. 6A, the downtubes 94 are shown inserted into wounds of the patient and attached to the screws 93, wherein the screws 93 are attached to the vertebrae of the patient. The rod 92, shown attached to the rod inserter 1, is held in a near vertical orientation approximately aligned with one of the downtubes 94 so as to be insertable into another minimally invasive wound in the patient adjacent a wound into which the downtube 94 has been inserted. To maintain vertical orientation of the rod 92, the lever 26 is squeezed to maintain pressure on the clamping head 60 via the inner shaft 30.

Figure 6B:
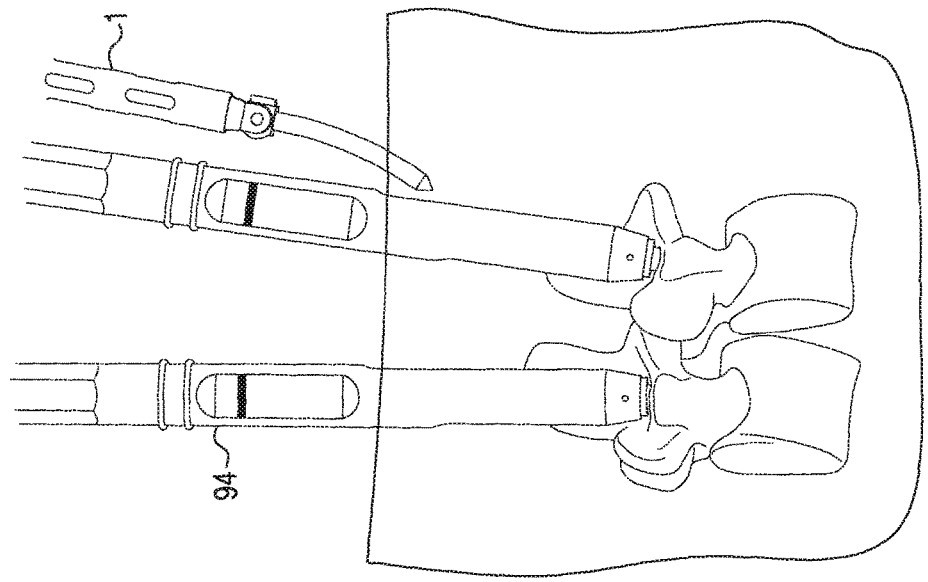
FIG. 6B is a perspective view of the rod inserter of FIG. 1 depicting a method of using the rod inserter.

In FIG. 6B, the rod 92 is shown pushed into an initial insertion within the downtube 94. Each downtube 94 has a longer side slot opposing a shorter side slot, wherein the rod 92 is initially pushed into insertion within the longer side slot while the lever 26 continues to be squeezed to prevent rotation of the clamping head 60.

In FIG. 6C, the rod 92 is shown partially inserted within the downtube 94, and has begun to pass through the downtube 94 via the longer side slot. At this stage, the lever 26 has been at least partially released so as to permit rotation of the clamping head 60 and attached rod 92 as the rod 92 contacts interior surfaces of the downtube 94 and the patient's soft tissue. With the lever 26 no longer squeezed to inhibit angulation of the rod 92, the interior surfaces of the downtube 94 and the patient's soft tissue that contact the rod 92 press against the rod 92 while the operator, such as a surgeon, applies downward pressure to the rod inserter 1 to drive the rod 92 further into the downtube 94 and associated pedicle screw 93. This downward pressure causes the rod 92 to angulate relative to the handle 20 and shafts 30, 40, and 50 of rod inserter 1 as the clamping head 60 rotates.

In FIGS. 6D and 6E, the rod 92 continues to angulate away from the near vertical orientation that was approximately aligned with (or coincident with) a longitudinal axis the rod inserter 1. As the rod 92 angulates with downward pressure on the rod inserter 1, the rod 92 approaches a second, adjacent downtube 94.

In FIG. 6F, angulation of the rod 92 can be locked again via actuation of the lever 26. With the rod 92 locked in a near horizontal orientation (or perpendicular orientation) with respect to the longitudinal axis of the rod inserter 1. The rod 92 can be inserted into the adjacent downtube 94 through the respective slot such that the rod 92 extends through both of the downtubes 94 and through the saddle or U-shaped portions of the heads of each of the pedicle screws 93.

In FIG. 6G, the end geometry 921 of the rod 92 is shown decoupled from the rod inserter 1 as a result of rotating the knob 10 along the threaded shaft 40 away from the collet 42a. Once decoupled, the rod inserter 1 can be removed from the patient through the wound while the rod 92 remains inserted through both downtubes 94 in a near horizontal orientation to bridge the screws 93 and join them together.

In the disclosed embodiment, various structures are applied to an instrument for insertion of a pedicle screw rod into pedicle screws fixed to a patient's vertebrae. However, the disclosed structures may alternatively be applied to or modified to cover any type of instrument configured to manipulate medical implants, including implantation of any rod structure for location adjacent a bone.

In the disclosed exemplary embodiments, the rod inserter 1 is configured for use by an operator with a certain dominant body side, such as right-handed or left-handed operators. However, the rod inserter can be configured for use by an operator having an alternate dominate body side by rotating a position of the lever about the handle.

Embodiments are also intended to include or otherwise cover methods of using and methods of manufacturing any or all of the elements disclosed above. The methods of manufacturing include or otherwise cover processors and computer programs implemented by processors used to design various elements of the rod inserter disclosed above.

While the subject matter has been described in detail with reference to exemplary embodiments thereof, it will be apparent to one skilled in the art that various changes can be made, and equivalents employed, without departing from the scope of the invention. For example, the number of various components can be changed without departing from the scope and spirit of the disclosed subject matter. Specifically, the shafts 30, 40, and 50 can include multiple shafts linked together to ensure appropriate length and shape. The clamping head 60 can be a single piece structure without a hinge, or a single piece structure that is hinged together via a living hinge, or can be multiple structures that are joined, or hinged together via a separate hinge structure that also includes several structures, such as guide structures and pin(s). In addition, the hex opening 69 of the clamping head 60 can be various shapes other than a hex shape and fall within the spirit of the presently disclosed subject matter. For example, the opening 69 can be circular, polygonal, non-symmetrical, elliptical, or various other shapes that are configured to mate with an associated end of rod 92. The opening 69 can also include lips and annular rings and other structures located therein to assist in location and connection of the rod 92 with the opening 69 in the clamping head 60.

A reversal of parts for most of the disclosed mating structures is also contemplated to be within the scope of the presently disclosed subject matter. For example, the threads of each of the threaded structures can be placed at different locations and on different structures to effect the same or similar motion for locking the rod within the clamping head 60. In addition, the location of specific structures can be reversed, for example, the knob 10 could be located at a proximal most portion of the handle 20 while the lever 26 could be located at a distal most portion of the handle 20.

The manner in which movement between each of the structures is facilitated can also be changed. For example, the roller bearing that facilitate rotational movement between the knob 10 and the outer shaft 50 can be replaced with other known structures or configuration that permit or facilitate such rotational movement, such as, for example, ball bearings, fluid bearings, tapered bearings, frictional surface bearings, and other known bearing structures or configurations, or no bearing.

Although the rod inserter 1 is disclosed as having a central through hole extending along the entire length of the rod inserter 1 to facilitate relative movement of the shafts 30, 40 and 50, the rod inserter 1 could be provided without such a central aperture and could rely on shafts that are configured as plates or other structures that run parallel with a longitudinal axis of the device but not coincident therewith.

The various structures of the rod inserter 1 can each be assembled from multiple parts and formed of different materials, or can each be constructed as a single homogeneous body of material, rather than an assembly of parts. In addition, the material can be a biocompatible material and/or antimicrobial. Suitable materials include but are not limited to stainless steel, titanium, other metals, metal alloys, ceramics, plastics, or superelastic shape memory alloys like Nitinol, or combinations thereof. The actuation mechanisms 10, 26 can be made from a plastic material to reduce the weight of the rod inserter 1, but can just as likely be made from stainless steel, titanium, other metals, metal alloys, ceramics, other plastics, or superelastic shape memory alloys like Nitinol, or combinations thereof. In addition, the spinal rod 93 and/or clamping head 60 can include a magnetic material to facilitate connection therebetween.

While the method of use of the rod inserter 1 and system is described in a chronological series of steps, the steps of the method need not be chronological. Instead, certain actions can occur simultaneously or in reverse or different order while remaining within the scope of the presently disclosed subject matter. Additional or different intervening steps can also be included in the method, and/or certain steps and functions can be omitted. For example, a step of angulating the spinal rod 92 can be excluded if the rod 92 and entry wound are sufficiently aligned to allow for direct insertion of the rod 92 into the pedicle screw 93.

The inner shaft 30 can be motivated to return to its original (non-actuated, non-locking) position through use of various structures, such as a simple spring biased return, a magnetic return, a pneumatic return, or other return structure. Likewise, if the shaft 40 were fitted with a lever instead of a knob for actuation, the return of shaft 40 could be motivated to return to its original (non-actuated, non-locking) position through use of various structures, such as a simple spring biased return, a magnetic return, a pneumatic return, or other return structure.

The collar 23 can include an inner surface that is circular, or if further prevention of rotation with respect to the handle 20 is desired (above that which set screw 22 can provide), the inner surface can be polygonal or elliptical or splined, etc. Alternatively, a flat surface can be provided on a portion of the handle 20 on which the set screw 22 contacts to secure the lever 26 to the handle 20 while also preventing relative rotation therebetween when the set screw 22 is tightened. As indicated above, the configuration of the lever 26 and handle 20 can permit a user to attach the lever 26 at various angular orientations with respect to the handle 20 (and with respect to the clamping head 60) to ensure a variety of orientations can be achieved for the lever 26 with respect to the remainder of the rod inserter 1. Of course, other locking devices or structures can be used instead of the set screw 22, such as a rotational collet lock, clip lock, or even weld or single piece construction of the handle 20 and collar 23/lever 26. In addition, the lever 26 can be configured in many different ways and remain within the scope of the presently disclosed subject matter, for example, the lever 26 could be configured to be more of a push button type device located at the proximal most end of the handle 20, can be a trigger type mechanism configured for actuation by a finger of a user within a finger hole, can be an electronically actuated device such as a solenoid or other motor driven lever. The lever 26 could modified to include pneumatic actuation structures, such as a piston rod/cylinder structure, to enhance the clamping force available for actuating the inner shaft 30.

The longitudinal axis is an axis that extends along a longest extent of a structure. The longest extent can be along a straight line and can also be along a curved line, or combination thereof. In addition, it should be noted that the term substantially as used herein describes a structure that is exactly at or almost at the specified parameter to the extent one of ordinary skill in the art would appreciate.

Although the method and structures are described for use in a minimally invasive surgery (MIS) technique, the disclosed embodiments could be used in open surgery and/or combinations of MIS and open surgery.

While the subject matter has been described in detail with reference to exemplary embodiments thereof, it will be apparent to one skilled in the art that various changes can be made, and equivalents employed, without departing from the scope of the invention. All related art references discussed in the above Description of the Related Art section are hereby incorporated by reference in their entirety.

What is claimed is:

1. A rod inserter for inserting a rod, comprising:
a handle having a proximal end and a distal end;
an extension structure extending from the handle, the extension structure having a distal end, a proximal end, and defining a longitudinal axis therebetween;
a first motion structure disposed intermediate the distal end of the handle and the proximal end of the extension structure;
a rod connection structure located at the distal end of the extension structure, the rod connection structure configured to rotate with respect to the extension structure, and to move toward and away from the longitudinal axis of the extension structure in order to connect and disconnect from the rod, wherein
the first motion structure is configured to rotate about the longitudinal axis of the extension structure to thereby move the rod connection structure toward the longitudinal axis of the extension structure when actuated; and
a second motion structure configured to prevent the rod connection structure from rotating with respect to the extension structure when actuated.

2. The rod inserter of claim 1, wherein the first motion structure is configured such that actuation of the first motion structure is accomplished by rotation of the first motion structure about the longitudinal axis of the extension structure, and wherein the second motion structure is configured such that actuation of the second motion structure is accomplished by rotation of the second motion structure about a rotational axis at an angle with respect to the longitudinal axis of the extension structure.

3. The rod inserter of claim 1, wherein
the first motion structure is a knob including internal threads, and the first motion structure further includes a linkage that has external threads located at a proximal end of the linkage, and the internal threads of the knob threadedly engage with the external threads of the linkage to cause the knob to move in a linear direction along the linkage when the knob is rotated.

4. The rod inserter of claim 3, wherein the linkage includes a shaft having an outer diameter, and the extension structure includes an outer shaft, wherein the shaft of the linkage extends through the outer shaft of the extension structure and the shaft of the linkage has an outer diameter that is greater than an outer diameter of the outer shaft of the extension structure.

5. The rod inserter of claim 4, wherein a distal end of outer shaft of the extension structure includes a transition region in which an inner diameter tapers from a first diameter to a second diameter to provide a taper, and wherein a distal end of the linkage has a mating taper that slidingly engages the taper of the outer shaft when the first motion structure is actuated.

6. The rod inserter of claim 3, wherein the linkage includes a collet structure located at a distal end of the linkage, and the collet structure is configured to squeeze the rod connection structure when the knob is moved in the linear direction away from the handle, wherein the rod connection structure securely grips the rod.

7. The rod inserter of claim 3, further comprising a bearing located between the rod connection structure and the linkage.

8. The rod inserter of claim 1, wherein
the second motion structure includes a lever rotatably connected adjacent the handle and configured to prevent rotation of the rod connection structure when actuated.

9. The rod inserter of claim 8, wherein the first motion structure includes a knob rotatably connected adjacent the handle and configured to cause the rod connection structure to lock the rod into the rod connection structure when the knob is rotated.

10. The rod inserter of claim 1, wherein the second motion structure includes a lever connected to the handle and includes an inner shaft extending though the handle, and rotation of the lever causes the inner shaft to move along the longitudinal axis of the extension structure to selectively engage the rod connection structure and prevent the rod connection structure from rotating with respect to the extension structure when the inner shaft engages the rod connection structure.

11. The rod inserter of claim 10, wherein
the inner shaft includes a distal end surface opposing the rod connection structure, and the distal end surface includes a textured pattern configured to lockingly engage the external surface of the rod connection structure to prevent rotation of the rod connection structure with respect to the extension structure when the textured pattern of the inner shaft matingly engages with the external surface of the rod connection structure.

12. The rod inserter of claim 10, wherein when the second motion structure is in a non-actuated state, a distal end surface of the inner shaft is spaced from away from the rod connection structure, wherein the rod connection structure freely rotates about the rotational axis.

13. The rod inserter of claim 12, wherein when the second motion structure is in an actuated state, a distal end of the inner shaft contacts the rod connection structure such that the rod connection structure is prevented from rotation about the rotational axis, and wherein when the first motion structure is in a non actuated state, a rod is unlocked and disengageable from the rod connection structure while the second motion structure is in the actuated state.

14. The rod inserter of claim 1, wherein the second motion structure is configured to prevent articulation of the rod connection structure when actuated, and allows for passive articulation of the rod connection structure when not actuated, and the first motion structure is actuatable when the second motion structure is actuated and when the second motion structure is not actuated.

15. A rod inserter for inserting a rod, comprising:
a handle having a proximal end, a distal end, and a longitudinal axis;
a lever actuation structure located adjacent the handle and having a rotational axis that is at an angle relative to the longitudinal axis of the handle;
an extension structure extending from the handle, the extension structure having a distal end, a proximal end, and an extension structure longitudinal axis;
a knob actuation structure located between the proximal end of the handle and the distal end of the extension structure; and
a rod connection structure located at the distal end of the extension structure, the rod connection structure configured to rotate about a rotational axis and with respect to the extension structure, and the rod connection structure including a first clamshell structure and a second clamshell structure, wherein the first clamshell structure and second clamshell structure are configured to move towards and away from each other in order to connect and disconnect from the rod, wherein
the knob actuation structure is configured such that when actuated in a first direction the first clamshell structure and the second clamshell structure move toward each other, and when actuated in a second direction different from the first direction, the first clamshell structure and the second clamshell structure move away from each other, and
the lever actuation structure is configured such that when actuated the first clamshell structure and the second clamshell structure are prevented from rotating about the rotational axis of the rod connection structure.

16. The rod inserter of claim 15, wherein the knob actuation structure includes a knob having internal threads, and a linkage that has external threads located at a proximal end of the linkage, and the internal threads of the knob threadedly engage with the external threads of the linkage to cause the knob to move in a linear direction along the linkage when the knob is rotated.

17. The rod inserter of claim 16, wherein the linkage includes a collet structure located at a distal end of the linkage, and the collet structure is configured to cause the first clamshell structure and the second clamshell structure to move towards each other when the knob is actuated in the first direction, and allows the first clamshell structure and the second clamshell structure to move away from each other when the knob is actuated in the second direction.

18. The rod inserter of claim 16, wherein the linkage includes a shaft having an outer diameter, and the extension structure includes an outer shaft, wherein the shaft of the linkage extends through the outer shaft of the extension structure, and the shaft of the linkage has an outer diameter that is greater than an outer diameter of the extension structure.

19. The rod inserter of claim 18, wherein a distal end of outer shaft of the extension structure includes a transition region in which an inner diameter tapers from a first diameter to a second diameter to provide a taper, and wherein a distal end of the linkage has a mating taper that slidingly engages the taper of the outer shaft when the knob actuation structure is actuated.

20. The rod inserter of claim 16, wherein the lever actuation structure includes an inner shaft running through a longitudinal axis of the linkage.

21. The rod inserter of claim 20, wherein when the lever actuation structure is in a non-actuated state, a distal end of the inner shaft is spaced away from the first clamshell structure and the second clamshell structure such that the first clamshell structure and the second clamshell structure freely rotate about the rotational axis of the rod connection structure.

22. The rod inserter of claim 20, wherein when the lever actuation structure is in an actuated state, a distal end of the inner shaft contacts the rod connection structure such that the rod connection structure is prevented from rotation about the rotational axis of the rod connection structure, and wherein when the knob actuation structure is in a non actuated state, a rod is unlocked and disengageable from the rod connection structure while the lever actuation structure is in the actuated state.

23. The rod inserter of claim 15, wherein the lever actuation structure includes an inner shaft, and rotation of the lever actuation structure causes the inner shaft to move along the longitudinal axis of the extension structure to ultimately contact with the rod connection structure to prevent the rod connection structure from rotating about the rotational axis of the rod connection structure.

24. The rod inserter of claim 15, wherein the lever actuation structure prevents articulation of the rod connection structure when actuated, and allows for passive articulation of the rod connection structure when not actuated, and the knob actuation structure is actuatable while the lever actuation structure is either actuated or not actuated.

25. The rod inserter of claim 15, wherein the knob actuation structure is disposed intermediate the distal end of the handle and the proximal end of the extension structure.

26. A method of using a rod inserter, comprising:
providing a rod inserter including,
a handle having a proximal end and a distal end,
a lever located adjacent the handle and having a rotational axis,
an extension structure extending from the handle, the extension structure having a distal end, a proximal end, and defining a longitudinal axis therebetween,
a knob located intermediate the distal end of the handle and the proximal end of the extension structure, and
a rod connection structure located at the distal end of the extension structure, the rod connection structure configured to rotate with respect to the extension structure;
actuating the lever to prevent the rod connection structure from rotating with respect to the extension structure; and
rotating the knob about the longitudinal axis of the extension structure to thereby cause a first portion of the rod connection structure to move with respect to the extension structure in a first direction, and to cause a second portion of the rod connection structure to move with respect to the extension structure in a second direction different from the first direction.

27. A rod inserter for inserting a rod, comprising:
a handle having a proximal end and a distal end;
an extension structure extending from the handle and defining an interior portion, the extension structure having a distal end, a proximal end, and a longitudinal axis;
a first motion structure disposed intermediate the distal end of the handle and the proximal end of the extension structure;
a rod connection structure located at the distal end of the extension structure, the rod connection structure configured to rotate with respect to the extension structure, and to move toward and away from the longitudinal axis of the extension structure in order to connect and disconnect from the rod, wherein
the first motion structure is configured to move the rod connection structure toward the longitudinal axis of the extension structure when actuated; and
a second motion structure configured to extend through the interior portion of the extension structure into abutment with the rod connection structure to thereby prevent the rod connection structure from rotating with respect to the extension structure when actuated.

* * * * *